(12) United States Patent
Bauer et al.

(10) Patent No.: US 8,219,212 B2
(45) Date of Patent: Jul. 10, 2012

(54) DISTAL PORTIONS FOR MEDICAL ELECTRICAL LEADS

(75) Inventors: Ryan T. Bauer, Brooklyn Park, MN (US); Yong D. Zhao, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1697 days.

(21) Appl. No.: 10/923,926

(22) Filed: Aug. 23, 2004

(65) Prior Publication Data

US 2006/0041299 A1    Feb. 23, 2006

(51) Int. Cl.
*A61N 1/372* (2006.01)

(52) U.S. Cl. .................................................. 607/119

(58) Field of Classification Search .............. 607/119, 607/122, 125, 126
See application file for complete search history.

(56) References Cited

U.S. PATENT DOCUMENTS

| | | | |
|---|---|---|---|
| 5,282,844 A | 2/1994 | Stokes | |
| 5,304,139 A | 4/1994 | Adams et al. | 607/122 |
| 5,423,772 A | 6/1995 | Lurie et al. | 604/282 |
| 5,433,729 A | 7/1995 | Adams et al. | 607/5 |
| 5,643,338 A * | 7/1997 | Bornzin et al. | 607/123 |
| 5,683,445 A | 11/1997 | Swoyer | 607/125 |
| 5,800,495 A | 9/1998 | Machek | |
| 5,902,330 A | 5/1999 | Ollivier | |
| 5,925,073 A | 7/1999 | Chastain et al. | 607/122 |
| 5,954,761 A | 9/1999 | Machek | |
| 5,999,858 A | 12/1999 | Sommer et al. | 607/122 |
| 6,038,482 A | 3/2000 | Vachon | |
| 6,055,457 A | 4/2000 | Bonner | |
| 6,144,882 A * | 11/2000 | Sommer et al. | 607/125 |
| 6,192,280 B1 | 2/2001 | Sommer | |
| 6,198,973 B1 | 3/2001 | Doan | |
| 6,240,321 B1 | 5/2001 | Janke | |
| 6,321,123 B1 | 11/2001 | Morris et al. | 607/122 |
| 6,377,856 B1 | 4/2002 | Carson | 607/122 |
| 6,430,449 B1 * | 8/2002 | Hsu et al. | 607/126 |
| 6,567,704 B2 | 5/2003 | Sundquist | |
| 6,584,362 B1 | 6/2003 | Scheiner et al. | 607/122 |
| 6,968,237 B2 * | 11/2005 | Doan et al. | 607/122 |
| 2002/0049485 A1 | 4/2002 | Smits | |
| 2002/0077685 A1 | 6/2002 | Sundquist | |

(Continued)

FOREIGN PATENT DOCUMENTS

EP    0778044 A    6/1997

(Continued)

OTHER PUBLICATIONS

International Search Report, PCT/US2005/029826, Jan. 12, 2005, 7 Pages.

(Continued)

*Primary Examiner* — Scott Getzow
*Assistant Examiner* — Amanda Patton
(74) *Attorney, Agent, or Firm* — Reed A. Duthler; Stephen W. Bauer

(57) ABSTRACT

A medical electrical lead includes a canted lead body distal portion extending from an approximately straight lead body proximal portion; the canted distal portion includes an approximately straight segment and a hump-like segment extending from a first end, in proximity to the approximately straight segment, to a second end. The lead further includes a first electrode coupled to the approximately straight segment of the distal portion and a second electrode coupled to the distal portion in proximity to a second end of the hump-like segment.

24 Claims, 4 Drawing Sheets

U.S. PATENT DOCUMENTS

| | | | |
|---|---|---|---|
| 2003/0009095 A1* | 1/2003 | Skarda | 600/374 |
| 2003/0050681 A1 | 3/2003 | Pianca et al. | 607/125 |
| 2003/0093138 A1 | 5/2003 | Osypka | |
| 2003/0109914 A1 | 6/2003 | Westlund et al. | 607/122 |
| 2003/0220676 A1 | 11/2003 | Helland | |
| 2003/0220677 A1 | 11/2003 | Doan et al. | 607/122 |
| 2004/0068312 A1 | 4/2004 | Sigg | |
| 2004/0122497 A1* | 6/2004 | Zhang et al. | 607/122 |
| 2004/0122498 A1* | 6/2004 | Zhang et al. | 607/122 |
| 2004/0133154 A1 | 7/2004 | Flaherty | |

FOREIGN PATENT DOCUMENTS

| | | |
|---|---|---|
| EP | 0788808 A | 8/1997 |
| WO | WO 00/56399 A | 9/2000 |
| WO | WO 2006023867 A | 3/2006 |

OTHER PUBLICATIONS

International Search Report, PCT/US2005/29989, Sep. 5, 2006, 3 Pages.

European Search Report, EP 05793869.8, May 11, 2007, 2 Pages.

* cited by examiner

DISTAL PORTIONS FOR MEDICAL ELECTRICAL LEADS

TECHNICAL FIELD

The present invention pertains to medical electrical leads and more particularly to pre-shaped distal lead portions.

BACKGROUND

Cardiac stimulation systems commonly include a pulse-generating device, such as a pacemaker or implantable cardioverter/defibrillator that is electrically connected to the heart by at least one medical electrical lead. A medical electrical lead delivers electrical pulses emitted by the pulse generator to the heart, stimulating the myocardial tissue via electrodes included on the lead. Cardiac signals may also be sensed by lead electrodes and conducted, via the lead, back to the device to monitor the electrical activity of the heart. These leads are coupled to the devices via connector terminals carrying one or more contact surfaces, which are in turn coupled to corresponding lead electrodes by elongate conductors extending within the lead.

In recent years, with the development of cardiac resynchronization therapy, pacing of the left ventricle has been achieved by implanting transvenous lead electrodes in the coronary venous system of the heart to stimulate an epicardial surface of the left ventricle. Precise placement of lead electrodes through the coronary veins is often difficult, forcing clinicians to work around sub-optimal pacing thresholds and/or unwanted extra-cardiac stimulation, for example phrenic nerve stimulation. Transvenous leads including a plurality of electrodes can provide an increased opportunity to provide more optimal pacing in that, once the lead is best positioned within a coronary vein, a choice of pacing sites is provided by the plurality of electrodes. Furthermore, pre-shaped distal portions of leads can enable stable placement of electrodes and enhance contact between the electrodes and electrically active cardiac muscle.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

Figure 1A:
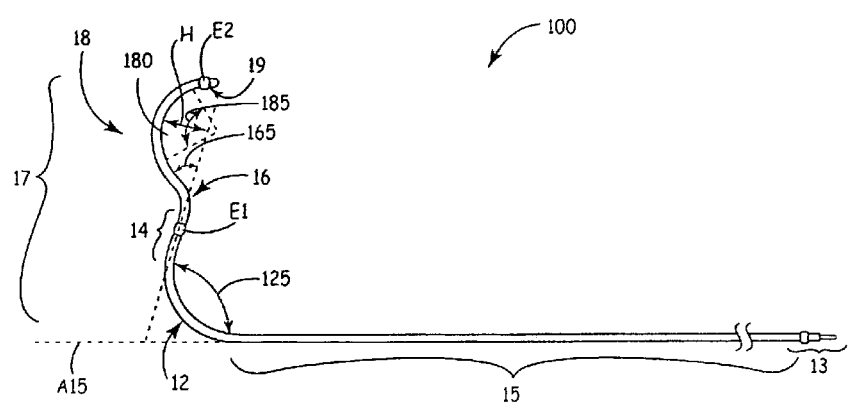
FIG. 1A is a plan view of a medical electrical lead according to one embodiment of the present invention.

FIG. 1A is a plan view of a medical electrical lead 100 according to one embodiment of the present invention. FIG. 1A illustrates lead 100 including an approximately straight proximal lead body portion 15, which is terminated at a proximal end by a lead connector 13, and a pre-formed distal lead body portion 17 extending distally from proximal portion 15. FIG. 1A further illustrates distal lead body portion 17 including a first arcuate segment 12 bending in a first direction, an approximately straight segment 14 extending from first arcuate segment 12, a second arcuate segment 16 extending from straight segment 14 and bending from the straight segment in a second, generally distal, direction, a third arcuate segment 18 bending from the second arcuate segment in a third, generally proximal, direction, and a distal tip segment 19 extending from the third arcuate segment 18. According to the illustrated embodiment of the present invention, lead 100 further includes a first electrode E1 coupled to approximately straight segment 14 and second electrode coupled to distal tip segment 19; the position of pre-formed curves of arcuate segments of distal portion 17 with respect to electrodes E1 and E2 provide for epicardial contact of electrodes E1 and E2 when implanted in a coronary vessel, as will be further described below.

FIG. 1A further illustrates angles 125, 165 and 185 of arcs included in arcuate segments 12, 16 and 18, respectively; according to some embodiments of the present invention, dimensions of the arcs are as indicated in Table 1.

TABLE 1

Arc Dimensions

| Arcuate Segment | Arc radius (inch) range | Arc angle range |
|---|---|---|
| 12 | ~0.2–~0.3 | Angle 125: ~45°–~90° |
| 16 | ~0.2–~0.4 | Angle 165: ~10°–~40° |
| 18 | ~0.1–~0.4 | Angle 185: ~60°–~100° |

Furthermore, a length of straight segment 14, according to some embodiments, is from approximately 0.2 to approximately 0.7 inch and a length of distal tip segment 19 is from approximately 0.05 inch to approximately 0.2 inch. According to one embodiment electrode E2 terminates distal tip segment 19, which may or may not extend proximally from electrode; according to another embodiment a portion of distal tip segment 19 extends distally from electrode E2 as illustrated by dashed lines in FIG. 1 and this extension may or may not be curved. Distal lead body portion 17 is alternately described as being canted, bending at angle 125 with respect to a longitudinal axis A15 of proximal portion 15 and including a hump-like segment, corresponding to segment 18, extending from approximately straight segment 14 and having a distal apex 180. According to one embodiment of the present invention, the arc of segment 18 has a chord length of approximately 0.4 inch to approximately 0.7 inch and distal apex 180 of segment 18 has a height H of approximately 0.1 inch to approximately 0.3 inch.

General construction details concerning lead 100, for example of arrangement of conductors and insulation, coupling of electrodes to conductors, and assembly of connector 13, are well known to those skilled in the art. Conductors coupling electrodes E1 and E2 to connector contacts of connector 13 may be side-by-side cables or coaxial coils, either of which may be formed of wires made from MP35N alloy; and insulation formed about conductors for electrical isolation may formed of polyurethane, fluoropolymers, silicone, polyimide or any combination thereof. Methods for pre-forming distal portion 17 include pre-forming of conductors extending therein and/or sheaths extending about the conductors; according to one method one or more sheaths extending between proximal lead body portion 15 and distal tip segment 17 are formed of polyurethane, which is heat set into the preformed curve; such a method is further described in U.S. Pat. No. 5,999,858, which is incorporated herein by reference.

Figure 1B:
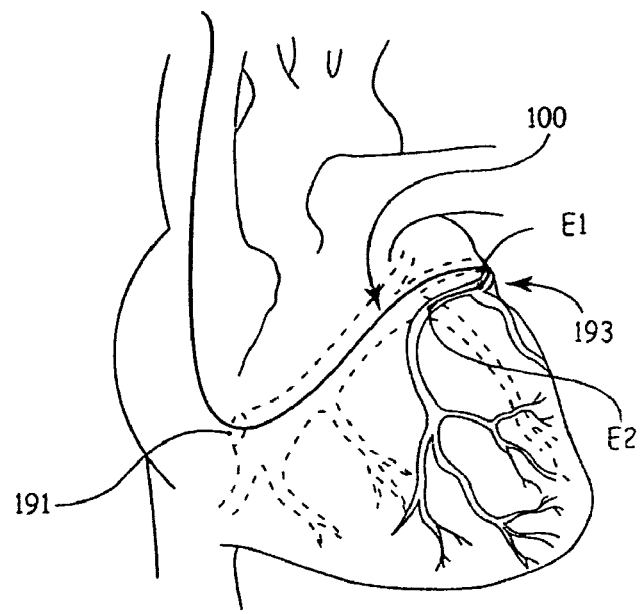
FIG. 1B is a schematic of the lead of FIG. 1A implanted in a coronary venous system from an anterior perspective.
Figure 1C:
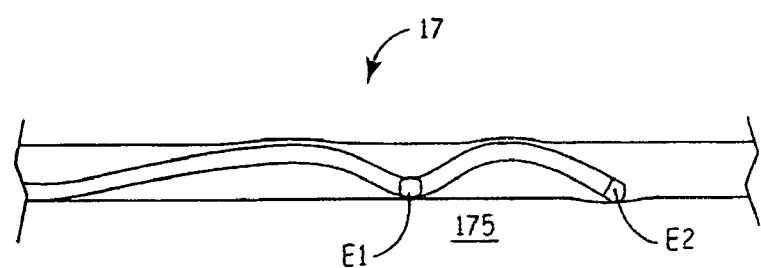
FIG. 1C is an enlarged view of a distal portion of the lead shown in FIG. 1A implanted within a coronary vein.

FIG. 1B is a schematic of lead 100 implanted in a coronary venous system 193, and FIG. 1C is an enlarged view of distal lead body portion 17 therein. FIG. 1B illustrates lead 100 having been passed through a coronary sinus 191 into coronary vasculature 193 such that electrodes E1 and E2 are positioned for left ventricular pacing. According to some embodiments of the present invention both electrodes E1 and E2 are designed for pacing stimulation so that one of the two electrodes may be selected for ventricular pacing based on a preferred implant position; as illustrated in FIG. 1C, the pre-formed curvature of distal lead body portion 17 assures that both electrodes E1 and E2 contact a left ventricular epicardial surface 175. Electrodes E1 and E2 may each have a surface area ranging between approximately 2 square millimeters and approximately 10 square millimeters and may be formed from any suitable material known to those skilled in the art, for example platinum-iridium and titanium. Dashed lines in FIG. 1C show an alternate distal lead body portion wherein a pre-formed hump (i.e. segment 18, FIG. 1A) is not included in order to illustrate a need for the hump when two electrodes are included in the distal lead body portion. FIG. 1C also shows how canted distal portion 17 serves to force electrode E2 into contact with epicardial surface 175.

FIG. 1C further illustrates that pre-formed segments 12, 16 and 18 (FIG. 1A) of distal portion 17 are flexible to bend in compliance with external forces such as that applied by the vessel walls of coronary vasculature 193. These segments may also be bent in compliance with an internal force applied by a stylet inserted within a lumen of lead 100.

Figure 2:
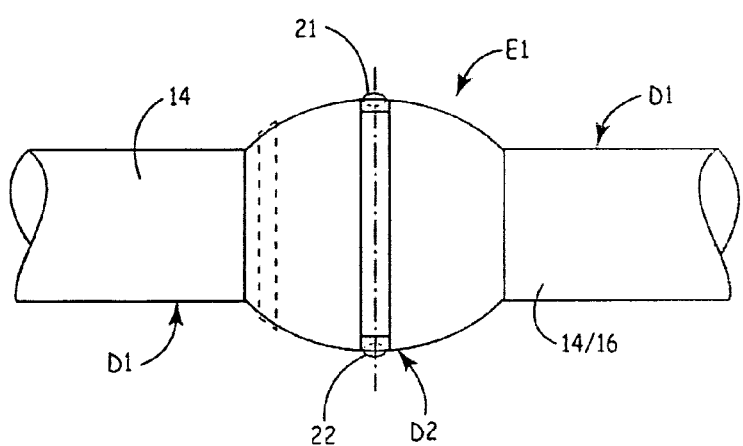
FIG. 2 is an enlarged detailed plan view of a lead electrode assembly according to one embodiment of the present invention.

FIG. 2 is an enlarged detailed plan view of a lead electrode assembly, corresponding to first electrode E1 illustrated in FIGS. 1A-C, according to one embodiment of the present invention. FIG. 2 illustrates approximately straight segment 14 of distal lead body portion 17 extending away from electrode E1 toward segment 12 (FIG. 1A); E1 may be positioned along segment 14 such that segment 14 further extends in an opposite direction from electrode E1, or such that electrode E1 is in close proximity or adjacent to second arcuate segment 16 (thus segment 14/16 indicated in FIG. 2).

FIG. 2 further illustrates electrode E1 including a central portion having a maximum diameter D2 that is greater than diameters D1 and D1' of segments 14 and 14/16, respectively, while either end of electrode E1 is approximately flush with diameters D1 and D1'. According to some embodiments of the present invention, a ratio of diameter D2 to diameters D1' and D1' is from approximately 1.1 to approximately 1.6. It is likely that an active outer surface of electrode E1 in proximity to D2 will make best contact with epicardial tissue, for example epicardial surface 175 illustrated in FIG. 1C.

According to the illustrated embodiment the active outer surface of electrode E1 has a generally arcuate profile and includes a recess 21, approximately aligned with a longitudinal center of electrode E1 and in which a therapeutic or bioactive agent 22 is held, agent 22 being adapted to disperse out from recess 21 upon implantation of electrode E1. According to an alternate embodiment, a recess holding an agent is offset from the longitudinal center of E1, as illustrated in FIG. 2 with dashed lines in proximity to segment 14. Although FIG. 1 illustrates recess extending about a circumference of electrode E1, alternate embodiments of the present invention include recesses, of a generally macroscopic scale, which are discrete in nature and of various orientations. Other dashed lines in FIG. 2 illustrate alternate profiles of agent 22 including arcuate and flat profiles which may be either protruding, flush or recessed with respect to adjacent outer surface of electrode E1. According to one set of embodiments of the present invention, agent 22 is embedded in a polymer matrix, and, according to a particular embodiment, agent 22 is an anti-inflammatory agent such as a steroid, for example dexamethasone sodium phosphate, dexamethasone acetate, or beclomethasone diproprionate, embedded in a polyurethane or silicone matrix such that the steroid may elute from the matrix to prevent inflammation at the electrode contact site. Methods for forming such compounds for application in embodiments of the present invention are well known to those skilled in the art. According to another set of embodiments, a surface of recess 21 includes a microstructure in which agent 22 is embedded, for example a platinized surface in which beclomethasone is embedded.

Figure 3:
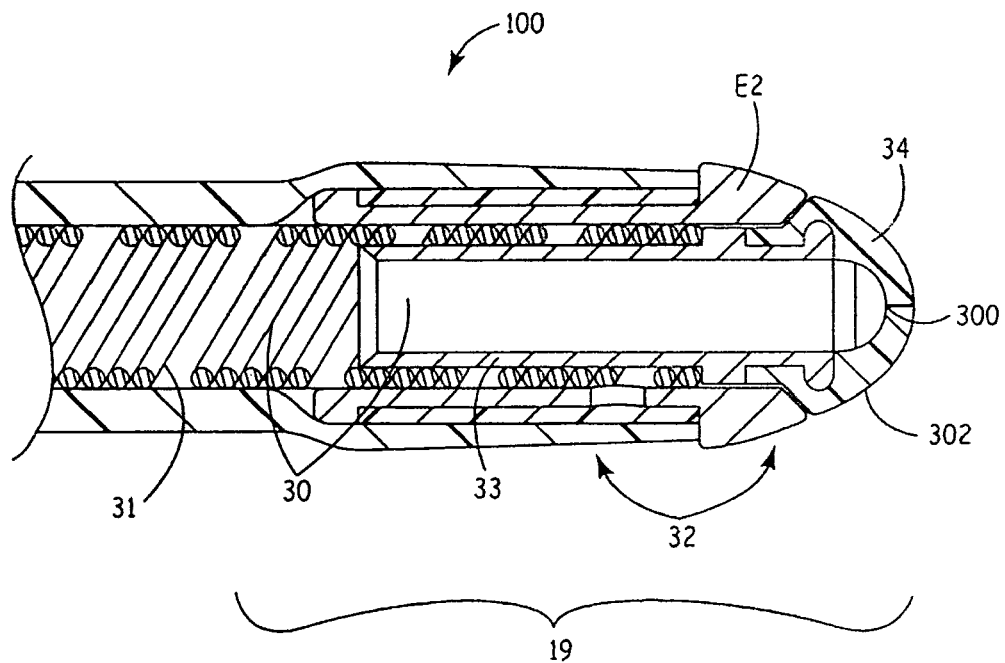
FIG. 3 is an enlarged detailed section view of another lead electrode assembly according to another embodiment of the present invention.

FIG. 3 is an enlarged detailed section view of another lead electrode assembly, corresponding to second electrode E2 illustrated in FIGS. 1A-C, according to another embodiment of the present invention. FIG. 3 illustrates lead 100 including a lumen 30 formed by a conductor coil 31 and a core 33 to which conductor coil 31 and electrode E2 are coupled; lumen 30 is terminated at a distal end of distal tip segment 19 with a resilient element 34 mounted upon core 33 and adjacent to electrode E2. According to the illustrated embodiment, element 34 is generally cup shaped and includes an outer surface 302, which forms a portion of an external surface 32 of distal tip segment 19 of distal lead body portion 17 (FIG. 1A), and an inner surface 300 adapted both to seal off lumen 30 and to spread apart to allow passage of an elongate member, for example a guide wire, by nature of the resiliency of element 34. U.S. Pat. No. 6,192,280 describes in part the assembly illustrated in FIG. 3 and is incorporated herein in its entirety. According to some embodiments of the present invention, element 34 further includes a therapeutic or bioactive agent embedded therein which is adapted to disperse out from outer surface 302 upon implantation of lead 100. According to one embodiment, the agent is an anti-inflammatory agent such as a steroid, for example dexamethasone sodium phosphate, dexamethasone acetate, or beclomethasone diproprionate, and element 34 is formed by transfer molding a blend of the steroid (10%-50% by weight) and a silicone rubber, according to methods known to those skilled in the art of silicone molding.

In the foregoing detailed description, the invention has been described with reference to specific embodiments. However, it may be appreciated that various modifications and changes can be made without departing from the scope of the invention as set forth in the appended claims. For example, the inventive electrode assemblies described herein are not limited to the lead body embodiments described herein and may be incorporated in many types of medical electrical systems. Furthermore, although embodiments of the present invention have been described herein in the context of cardiac pacing from the coronary venous vasculature, the scope of the present invention is not limited to this particular application and embodiments of the present invention may be applied to other vessel-like environments.

What is claimed is:

1. A medical electrical lead, comprising:
a proximal lead body portion having a proximal connector and extending in a distal direction from the proximal connector;
a distal lead body portion extending from the proximal lead body portion and comprising:
a first arcuate segment extending from the proximal lead body portion and bending in a first direction,
an approximately straight segment extending from the first arcuate segment and away from the longitudinal axis of the proximal lead body portion,
a second arcuate segment extending from the approximately straight segment and bending in a second generally distal direction,
a third arcuate segment extending from the second arcuate segment and bending in a third generally proximal direction, which is also generally opposite the second direction, the third arcuate segment having an apex directed generally in the distal direction,
a distal tip segment extending from the third arcuate segment;
a first electrode positioned along the approximately straight segment of the lead body distal portion; and
a second electrode coupled to the distal tip segment of the lead body distal portion.

2. The lead of claim 1, wherein the first arcuate segment of the lead body distal portion includes an arc having an angle of approximately 45 degrees to approximately 90 degrees.

3. The lead of claim 1, wherein the first arcuate segment of the lead body distal portion includes an arc having a radius of approximately 0.2 inch to approximately 0.3 inch.

4. The lead of claim 1, wherein the approximately straight segment of the lead body distal portion extends for a length of approximately 0.2 inch to approximately 0.7 inch.

5. The lead of claim 1, wherein the second arcuate segment of the lead body distal portion extends at an angle of approximately 10 degrees to approximately 40 degrees away from a longitudinal axis of the approximately straight segment.

6. The lead of claim 1, wherein the second arcuate segment of the lead body distal portion includes an arc having a radius of approximately 0.2 inch to approximately 0.4 inch.

7. The lead of claim 1, wherein the third arcuate segment of the lead body distal portion includes an arc having an angle of approximately 60 degrees to approximately 100 degrees.

8. The lead of claim 1, wherein the third arcuate segment of the lead body distal portion includes an arc having a radius of approximately 0.1 inch to approximately 0.4 inch.

9. The lead of claim 1, wherein the distal tip segment of the lead body distal portion is elongate and approximately straight.

10. The lead of claim 9, wherein a length of the distal tip segment is approximately 0.05 inch to approximately 0.2 inch.

11. The lead of claim 1, wherein the first electrode is located adjacent to the first arcuate segment.

12. The lead of claim 1, wherein the first electrode is located adjacent to the second arcuate segment.

13. The lead of claim 1, wherein the second electrode is located adjacent to the third arcuate segment.

14. The lead of claim 1, wherein the second electrode terminates the distal tip segment of the lead body distal portion.

15. The lead of claim 1, wherein the second electrode is located adjacent to a distal end of the distal tip segment of the lead body distal portion.

16. A medical electrical lead, comprising:
a lead body proximal portion having a proximal connector and extending in a distal direction from the proximal connector;
a canted lead body distal portion extending from the proximal lead body portion and including an approximately straight segment extending away from a longitudinal axis of the lead body proximal portion and a hump-like segment extending from the approximately straight segment in a direction away from the longitudinal axis of the lead body proximal portion, the hump-like segment including an apex directed in the distal direction;
a first electrode positioned along the approximately straight segment of the lead body distal portion; and
a second electrode coupled to the lead body distal portion and located along the hump-like segment.

17. The lead of claim 16, wherein the canted distal portion bends at an angle away from the longitudinal axis of the lead body proximal portion of approximately 90 degrees to approximately 135 degrees.

18. The lead of claim 16, wherein the approximately straight segment of the canted lead body distal portion extends for a length of approximately 0.2 inch to approximately 0.7 inch.

19. The lead of claim 16, wherein the distal apex of the hump-like segment is offset approximately 0.1 inch to approximately 0.3 inch in the distal direction from a longitudinal axis of the approximately straight segment.

20. The lead of claim 16, wherein the hump-like segment forms an arc having a maximum chord length of approximately 0.4 inch to approximately 0.7 inch.

21. The lead of claim 16, wherein the first electrode is located adjacent to the hump-like segment.

22. A medical electrical lead, comprising:
a proximal lead body portion having a proximal connector and extending in a distal direction from the proximal connector;
a distal lead body portion extending from a first segment of the proximal lead body portion and comprising:
a first arcuate segment extending from the proximal lead body portion and forming a first angle with the first segment of the proximal lead body portion of up to approximately ninety degrees,
an approximately straight segment extending from the first arcuate segment,
a second arcuate segment extending from the approximately straight segment and forming a second angle of approximately 140 degrees to 170 degrees with the approximately straight segment,
a third arcuate segment extending from the second arcuate segment and bending in a generally proximal direction, the third arcuate segment having an apex directed generally in the distal direction;
a distal tip segment extending from the third arcuate segment;
a first electrode positioned along the approximately straight segment of the lead body distal portion; and
a second electrode coupled to the distal tip segment of the lead body distal portion.

23. A medical electrical lead, comprising:
a proximal lead body portion having a proximal connector and extending in a distal direction from the proximal connector;

a distal lead body portion extending from the proximal lead body portion and comprising:

a first arcuate segment extending from a first segment of the proximal lead body portion and bending in a first direction, an approximately straight segment extending from the first arcuate segment and away from the longitudinal axis of the proximal lead body portion, a second arcuate segment extending from the approximately straight segment and bending from the approximately straight segment in a second generally distal direction, a third arcuate segment extending from the second arcuate segment and bending from the second arcuate segment in a third generally proximal direction, which is also generally opposite the second direction, the third arcuate segment having an apex directed generally in the distal direction, a distal tip segment extending from the third arcuate segment;

a first electrode positioned along the approximately straight segment of the lead body distal portion; and a second electrode coupled to the distal tip segment of the lead body distal portion.

24. The medical electrical lead of claim 23, wherein the first arcuate segment bends to form an angle of approximately 45 degrees to approximately 90 degrees with the first segment of the proximal lead body portion.

* * * * *